United States Patent [19]

Tan et al.

[11] Patent Number: 5,633,337

[45] Date of Patent: May 27, 1997

[54] AROMATIC BENZOBISAZOLE POLYMERS AND COPOLYMERS INCORPORATING DIPHENYLAMINO MOIETIES

[75] Inventors: Loon-Seng Tan, Centerville, Ohio; Kasturi R. Srinivasan, Niwot, Colo.

[73] Assignee: The United States of America as represented by the Secretary of the Air Force, Washington, D.C.

[21] Appl. No.: 613,787

[22] Filed: Feb. 23, 1996

Related U.S. Application Data

[63] Continuation-in-part of Ser. No. 380,175, Jan. 26, 1995, Pat. No. 5,536,866.

[51] Int. Cl.$^6$ .................................................. C08G 75/32
[52] U.S. Cl. ........................ 528/183; 528/186; 528/337; 528/339; 528/342
[58] Field of Search .................................. 528/183, 186, 528/337, 339, 342

[56] References Cited

U.S. PATENT DOCUMENTS 5,098,988  3/1992  Tsai et al. .............................. 528/183

OTHER PUBLICATIONS

T. D. Dang, S. J. Bai, D. P. Heberer, F. E. Arnold and R. J. Spry, "Ionic Conductivity of Conjugated Water-Soluble Rigid-Rod Polymers", *Journal of Polymer Science: Part B: Polymer Physics*, vol. 32, 1941–1950 (1993).

Patricia A. DePra, John G. Gaudiello and Tobin J. Marks, "Conductive Polymers Based upon Rigid-Rod Ultrahigh-Modulus Macromolecules. Electrochemical Doping of Poly(p-phenylenebenzobisthiazole-2,6-diyl)(PBT)", *Macromolecules* 1988, 2295–2297.

J. H. Gorvin, "The Synthesis of Di-and Tri-arylamines through Halogen Displacement by Base-activated Arylamines: Comparison with the Ullmann Condensation", *J. Chem. Soc. Perkin Trans I*, 1988, 1331–1335.

C. Y-C Lee, J. Swiatkiewicz, P. N. Prasad, R. Mehta and S. J. Bai, "Third order non-linear optical properties of poly-p-phenylene benzobisthiazole and its novel composite with Zytel processed via methane sulfonic acid solution extrusion", *Polymer*, 1991, vol. 32, No. 7, 1195–1199.

K. R. Srinivasan and L-S Tan, "Synthesis and Characterization of Aromatic Benzobisazole Polymers Incorporated With Diphenylamino Moieties", *Polymer Preprints*, vol. 36(1), 445–446, Apr. 1995.

K. R. Srinivasan, L-S Tan, S. J. Bai and R. J. Spry, "Synthesis and Conductivity of Aromatic Benzobishiazole Copolymers With Main-Chain Diphenylamino Units", *Polymer Preprints*, vol. 36(2), 249–250, Aug. 1995.

C. S. Wang, J. Burkett, C. Y-C Lee and F. E. Arnold, "Structure and Electrical Conductivity of Ion-Implanted Rigid-Rod and Ladder Polymers", *Journal of Polymer Science: Part B: Polymer Physics*, vol. 31, 1799–1807 (1993).

*Primary Examiner*—James J. Seidleck
*Assistant Examiner*—P. Hampton-Hightower
*Attorney, Agent, or Firm*—Charles E. Bricker; Thomas L. Kundert

[57] ABSTRACT

A polymer having repeating units of the formula:

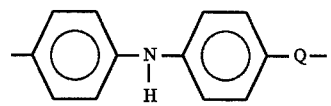

wherein Q is

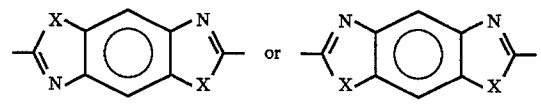

wherein X is —NH—, —S— or —O—.

A copolymer having repeating units of the formula:

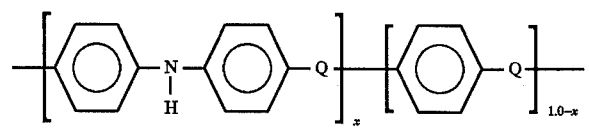

wherein x has a value of 0.01 to 0.99 and Q is

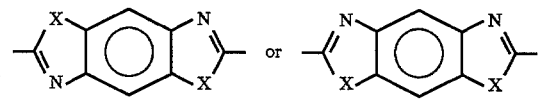

wherein X is —NH—, —S— or —O—.

8 Claims, No Drawings

AROMATIC BENZOBISAZOLE POLYMERS AND COPOLYMERS INCORPORATING DIPHENYLAMINO MOIETIES

RIGHTS OF THE GOVERNMENT

The invention described herein may be manufactured and used by or for the Government of the United States for all governmental purposes without the payment of any royalty.

CROSS-REFERENCE TO RELATED APPLICATION

This is a continuation-in-part of U.S. application Ser. No. 08/380,175, Filed Jan. 26, 1995 now U.S. Pat. No. 5,536,866, issued Jul. 16, 1996.

BACKGROUND OF THE INVENTION

The present invention relates to new di- and tri-arylamine-based dinitrile and dicarboxylic acid monomers. This invention further relates to new benzobisazole polymer and copolymer compositions containing an electron-rich diarylamine group for multifunctional high performance applications.

Rigid-rod poly(benzobisazole) (PBZ) polymers are well-known for their superior mechanical properties and high-temperature capability which are better than the state-of-the-art Aramids (e.g. Kevlar). The PBZ group includes poly(benzobisoxazole)(PBO), poly(benzobisthiazole) (PBT) and poly(benzobisimidazole) (PBI) polymers. These polymers have been heralded as the next-generation structural materials.

It is known that isotropic and biaxially oriented PBZ films can be rendered electrically conductive via $^{84}Kr^+$-ion implantation. Conductivity as high as 100 S/cm for biaxial oriented film has been achieved. It is also known that a PBZ film can be reduced electrochemically to a conductivity of about 20±10 S/cm. This is in accord with the fact that PBZ is known to be a π-deficient aromatic system as evidenced by both chemical and spectroscopic studies. Certain derivatized PBZ polymers have also exhibited $\chi^{(3)}$ non-linear optical (NLO) properties and ionic conductivity.

We have found that the conductivity of PBZ polymers and copolymers can be enhanced by incorporating di- and tri-arylamine moieties therein.

It is therefore an object of the present invention to provide novel di- and tri- arylamine-based dinitrile and dicarboxylic acid monomers.

It is another object of the present invention to provide novel benzobisazole polymers and copolymers containing functional groups for multifunctional high performance applications.

Other objects and advantages of the present invention will be apparent to those skilled in the art.

SUMMARY OF THE INVENTION

In accordance with the present invention there are provided novel triarylamino-based dinitrile and dicarboxylic acid monomers as represented by the formula:

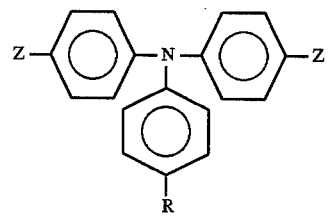

wherein Z is —CN or —COOH and R is selected from the group consisting of —H, —$CH_3$, —$N(CH_3)_2$ and —OH.

There are also provided novel diarylamino-based dinitrile and dicarboxylic acid monomers as represented by the formula:

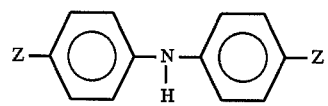

wherein Z is —CN or —COOH.

DETAILED DESCRIPTION OF THE INVENTION

The triarylamine dinitrile monomers can be prepared by the cesium fluoride-promoted, aromatic nucleophilic displacement reaction of 4-fluorobenzonitrile by aniline and certain para-substituted derivatives thereof, in an aprotic polar solvent. The dicyanotriarylamine can be prepared as shown by the following reaction scheme:

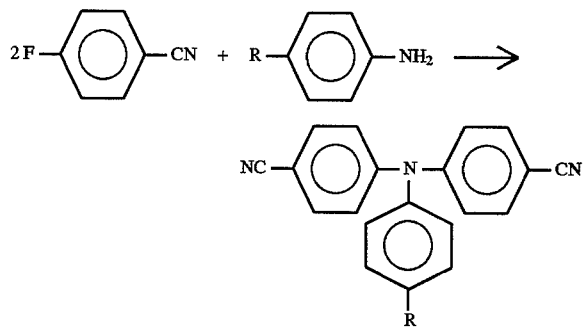

Suitable solvents for this reaction include dimethyl sulfoxide (DMSO), dimethyl acetamide (DMAc), N-methyl pyrrolidinone (NMP) and the like. In general, the reaction requires heating at reflux for about 1 to 24 hours. As shown in the Examples which follow, the monomers can be recovered from the reaction mixture using procedures known in the art. For example, the reaction mixture can be precipitated in water, then the crude product can be purified by recrystallization in appropriate solvents. Alternatively, the reaction mixture can be concentrated on a rotary evaporator, followed by vacuum-distillation of the unreacted starting materials and residual solvent. The remaining residue can then be purified by recrystallization.

The diarylaminedinitrile monomer can be prepared by the reaction of 4-aminobenzonitrile with 4-fluorobenzonitrile at room temperature for about 24 hours, in the presence of potassium tert-butoxide (KOBu$^t$) in an aprotic solvent, preferably a sulfur-free, polar aprotic amide solvent such as N, N-dimethylacetamide (DMAc), N-methylpyrrolidinone (NMP) or, N,N-dimethylformamide (DMF). Upon alkaline hydrolysis, it can be transformed into 4,4'-dicarboxydiphenylamine. The dinitriles are readily converted to the corresponding dicarboxylic acid monomers under either acidic or basic conditions. Acidic hydrolysis comprises, for example, refluxing the dicyano compound in a mixture of acetic acid and HBr. Basic hydrolysis comprises, for example, refluxing the dicyano compound in a mixture of KOH, ethylene glycol and water, followed by acidic work-up.

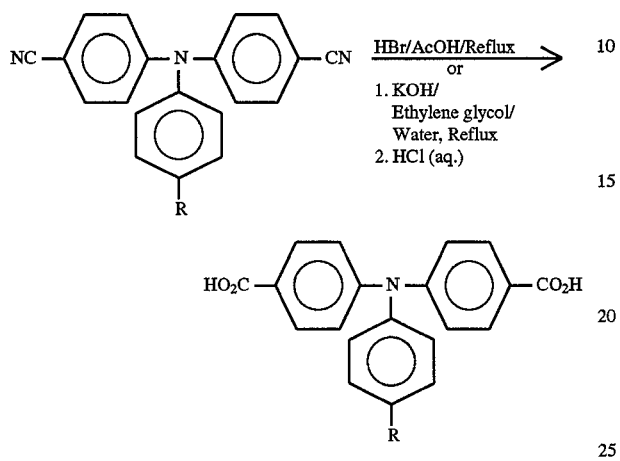

The di- and tri-arylamino-based dinitrile and dicarboxylic acid monomers of this invention are useful in the preparation of benzobisoxazole, benzobisimidazole and benzobisthiazole polymers and copolymers. The polymers are prepared by the polycondensation of a tetraaminobenzene, a diaminobenzenedithiol or a diaminobenzenediol with a dicyano- or dicarboxylic acid di- or tri-arylamine, as shown below. Briefly, the polymerization process comprises the following steps: (i) dehydrochlorination of a tetraaminobenzene tetrahydrochloride, a diamino-benzenedithiol dihydrochloride or a diamino-benzenediol dihydrochloride in the presence of a dinitrile or dicarboxylic acid monomer in 77% polyphosphoric acid (PPA) at 50°–65° C.; (ii) addition of $P_2O_5$ to raise the $P_2O_5$ content of the medium to 83%; (iii) chain propagation and cyclodehydration; and (iv) precipitation of the polymer into water, followed by washing the polymer with ammonium hydroxide and with hot water and drying the polymer in vacuum at 110° C. The polymerization reactions are, for example:

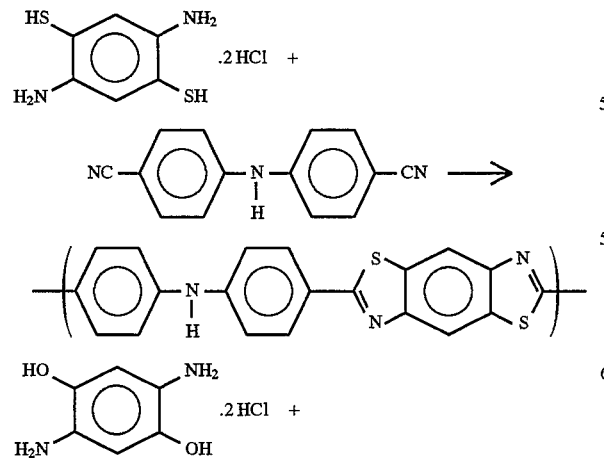

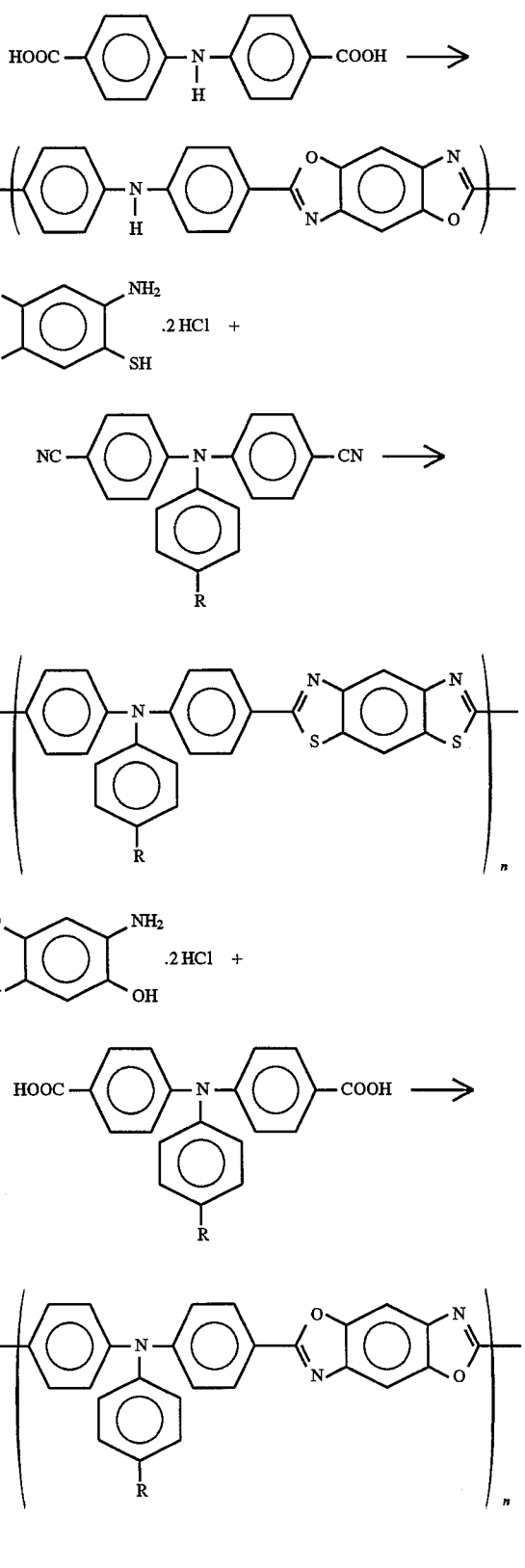

The copolymers are prepared in similar manner, for example:

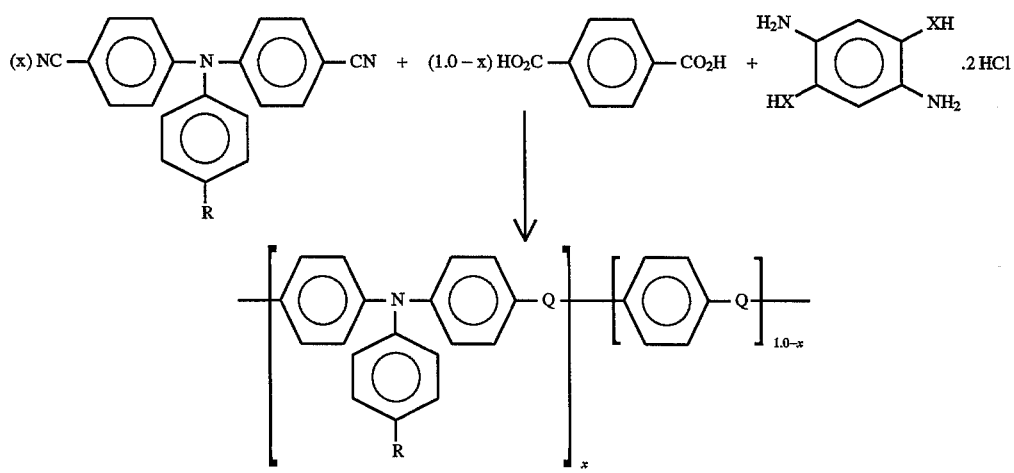

wherein x has a value of 0.01 to 0.99 and Q is

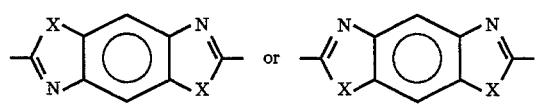

wherein X is —NH—, —S— or —O—.

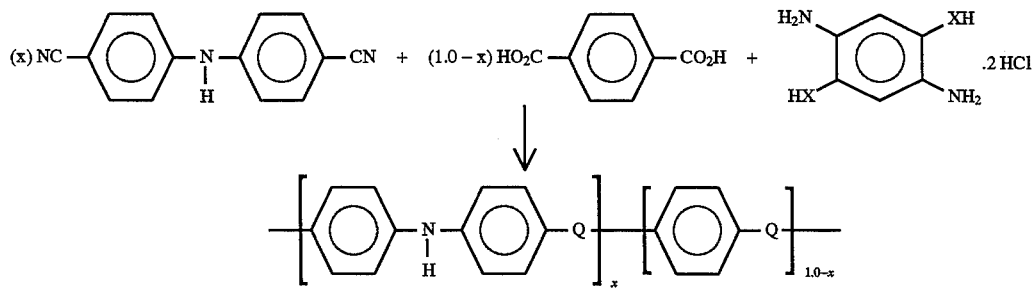

wherein x and Q are as defined above.

These polymers and copolymers can be cast into film or fiber at the time of precipitation; alternatively, they can be precipitated, washed and dried, then dissolved in a strong acid, such as methanesulfonic acid (MSA), then spin-cast into fibers or cast into film. These polymers and copolymers exhibit increased electrical conductivity, as compared to poly(p-phenylene benzobisazole) polymers. The polymers and copolymers can be treated with iodine to further increase their electrical conductivity. Preparation of the triarylamine polymers and copolymers is described in application Ser. Nos. 08/380,177 and 08/380,170, respectively, filed Jan. 26, 1995. Preparation of the diarylamine polymers and copolymers is described in the Examples which follow.

The following examples illustrate the invention:

EXAMPLE I

4,4'-Dicyanotriphenylamine

In a three neck round bottom flask fitted with a mechanical stirrer, nitrogen inlet and a condenser was placed aniline (2.00 g, 21.47 mmol), 4-fluorobenzonitrile (5.70 g, 47.06 mmol), finely ground cesium fluoride (9.00 g, 59.25 mmol) and 80 ml DMSO. The reaction mixture turned yellow from colorless on heating. The mixture was held at 100° C. for 2 h, and thin layer chromatography (TLC) of reaction mixture revealed only starting materials. The mixture was heated at 150°–155° C. for 2 h, at which stage TLC of the reaction mixture showed the appearance of a new compound. The temperature was increased to 185°–189° C. and the reaction mixture heated for 4 h. The greenish-black solution was cooled and poured over ice and stirred for 0.5 h. The resulting pale brown solid was filtered, washed several times with water and recrystallized from 2-propanol-acetone or methanol-water mixture to obtain a light yellow solid. Yield: (60%), m.p.: 191°–193° C. Elemental Analysis for $C_{20}H_{13}N_3$: Calcd.: C, 81.33%; H, 4.44%; N, 14.23%. Found: C, 81.37%; H, 4.49%; N, 14.20%. IR (KBr; cm$^{-1}$): 3060 (sp$^2$C-H), 2221 (CN). Mass spectrum: m/e: 295 (M$^+$, 100%).

EXAMPLE II

4,4'-Dicyano-4"-methyl-triphenylamine

In a 250 ml three neck round bottom flask was placed 4-methylaniline (4.00 g, 37.32 mmol), 4-fluorobenzonitrile (9.04 g, 74.64 mmol), cesium fluoride (11.50 g, 75.70 mmol) and 100 ml DMAc. The light brown solution was stirred and heated slowly. On refluxing the solution for 1 h, TLC of the sample showed disappearance of the 4-methylaniline. The brown solution was refluxed for an additional 4 h, cooled and precipitated in water. The brown organic layer was extracted with ethyl acetate, washed with water, dried and roto-evaporated to obtain a yellow oil. On addition of a few drops of 1 M hydrochloric acid (HCl), the yellow oil solidified. The solid was washed with water, dried and recrystallized from methanol-acetone-water to obtain a off-white crystalline solid. Yield: 4.00 g (35%), m.p.: 215°–216°

C. Elemental Analysis for $C_{21}H_{15}N_3$: Calcd.: C, 81.53%; H, 4.89%; N, 13.58%. Found: C, 81.30%; H, 4.80%; N, 13.38%. IR (KBr; cm$^{-1}$): 3070 (sp$^2$C–H), 2982 (sp$^2$C–H), 2230 (CN), 1600, 1500 (C=C). Mass Spectrum: m/e: 309 (M$^+$, 100%)

EXAMPLE III 4,4'-Dicyano-4"-N,N-dimethylamino-triphenylamine

In a 250 ml three neck round bottom flask fitted with a mechanical stirrer, nitrogen inlet and a condenser was placed N,N-dimethyl-1,4-phenylenediamine (4.00 g, 29.37 mmol), 4-fluorobenzonitrile (7.20 g, 59.47 mmol), finely ground cesium fluoride (9.05 g, 59.57 mmol) and 80 ml DMSO. The green solution was stirred at 100° C. for 3 h, and TLC of the reaction mixture revealed only starting materials. The mixture was heated at 150° C. for 3 h, and then heated at reflux for 16 h. The greenish-black solution was cooled and precipitated in ice, and stirred for 0.5 h. The crude green solid was recrystallized from 2-propanol-acetone or methanol-water mixture to obtain green-yellow needles. Yield: 4.98 g (50%), m.p.: 173°–175° C. Elemental Analysis for $C_{22}H_{18}N_4$: Calcd.: C, 78.08%; H, 5.36%; N, 16.56%. Found: C, 78.00%; H, 5.29%; N, 16.52%. IR (KBr, cm$^{-1}$): 3060 (sp$^2$C–H), 2850, 2790 (sp$^3$C–H), 2221 (CN). Mass Spectrum: m/e: 338 (M$^+$, 100%).

EXAMPLE IV 4,4'-Dicyano-4"-methoxy-triphenylamine

In a 250 ml three-necked, round-bottomed flask fitted with a nitrogen inlet, condenser and a magnetic stir-bar were placed 4-methoxyaniline (6.00 g, 48.70 mmol.), 4-fluorobenzonitrile (11.80 g, 97.43 mmol.), cesium fluoride (14.80 g, 97.43 mmol.) and 80 ml of NMP. The resultant mixture was heated at reflux for 16 h., cooled and then poured over ice. No precipitation occurred. Therefore, the solution was extracted with terahydrofurantoluene mixture. The extract was then dried over MgSO$_4$ and roto-evaporated to afford a brown oil. Upon removal of residual 4-fluorobenzonitrile and NMP, an off-white solid was obtained. It was washed with methanol and dried, and then recrystallized from acetone-methanol mixture. Yield: 7.00 g (44%), m.p. 173°–176° C. Elemental Analysis for $C_{21}H_{15}N_3O$: Calcd.: C, 77.52%; H, 4.65%; N, 12.91%. Found: C, 77.42%; H, 4.61%; N, 12.86%. IR (KBr, cm$^{-1}$): 3060 (sp$^2$C–H), 2956, 2864 (sp$^3$C–H), 2237 (CN). Mass Spectrum: m/e: 363 (M$^+$, 100%).

EXAMPLE V 4 4'-Dicarboxytriphenylamine

In a 100 ml round-bottomed flask equipped with a reflux condenser and a drying tube was placed 4,4'-dicyano-triphenylamine (1.00 g, 3.38 mmol.), followed by the addition of 15 ml of glacial acetic acid and 15 ml of 48% HBr. The light green slurry was then heated to reflux, at which point all the solid dissolved, resulting in a dark green solution. Reflux was continued for an additional hour. Thin layer chromatography of the reaction mixture indicated the absence of the starting dinitrile. The dark green solution was cooled to room temperature, poured into an ice-water mixture, and neutralized with 20% aqueous ammonium hydroxide. The crude product was collected on a fritted filter funnel, washed with copious amount of water, and suction-dried overnight. Recrystallization from aqueous methanol afforded the dicarboxylic acid as a light gray, crystalline solid. Yield: 1.00 g (89%), m.p. 174°–178° C. Elemental Analysis for $C_{20}H_{15}NO_4$: Calcd.: C, 72.06%; H, 4.53%; N, 4.20%. Found: C, 71.70%; H, 4.46%; N, 4.02%. Mass Spectrum: m/e: 334 (M$^+$, 100%).

EXAMPLE VI 4,4'-Dicarboxy-4"-N,N-dimethylamino-triphenylamine (via acidic hydrolysis)

In a 250 ml round-bottomed flask, equipped with a reflux condenser and a drying tube, was placed 4,4'-dicyano-4"-N,N-dimethylamino-tfiphenylamine (10.00 g, 29.55 mmol.), glacial acetic acid (40 mL) and aqueous hydrobromic acid (48%, 40 ml). The resulting light green-yellow slurry was stirred magnetically. Upon heating, it became green-brown. At reflux, the reaction mixture was completely homogeneous and very dark green. After an hour of reflux, thin layer chromatography of the reaction mixture, using 1:3 (v/v) ethyl acetate/hexane as an eluent, showed the absence of the starting dicyano compound. The reaction mixture was refluxed for another 3 hours, allowed to cool to room temperature, and poured into cold water. The gray precipitate was collected on a flitted filter funnel. Upon washing with 50% ammonium hydroxide, it became yellow. The crude product was then washed with copious amount of water and suction-dried overnight. Recrystallization of the crude product from aqueous methanol provided the dicarboxylic acid as a yellow, crystalline solid. Yield: 10.45 g (94%), m.p. 226°–227° C. Elemental Analysis for $C_{22}H_{20}N_2O_4$: Calcd.: C, 70.20%; H, 5.36%; N, 7.44%. Found: C, 70.02%; H, 5.28%; N, 7.33%. Mass Spectrum: m/e: 376 (M$^+$, 100%).

EXAMPLE VII 4,4'-Dicarboxy-4"-N,N-dimethylamino-triphenylamine (via basic hydrolysis)

In a 100 ml round-bottomed flask were placed 4,4'-dicyano-4"-N',N'-dimethylamino-triphenylamine (5.00 g, 14.77 mmol.) and potassium hydroxide (3.32 g, 59.09 mmol.) and 40 ml of ethylene glycol. The resultant slurry was heated at reflux for 6 h. During reflux, the reaction mixture became completely clear and greenish yellow and water was added to the reaction mixture at a regular interval. The greenish yellow solution was cooled, poured over ice, and neutralized with 3 N hydrochloric acid. The crude product was isolated by filtration, dried and recrystallized from aqueous methanol and then from ethanol/acetonitrile to provide the desired diacid as a dark green crystalline solid. Yield: 5.11 g (92%), m.p. 262°–264° C. Elemental Analysis for $C_{22}H_{20}N_2O_4$: Calcd.: C, 70.20%, H, 5.35%; N, 7.44%. Found: C, 70.08%; H, 5.29%; N, 7.30%. IR (KBr, cm$^{-1}$): 3500-2500 (OH), 1681 (C=O). Mass Spectrum: m/e:376 (M$^+$, 100%)

EXAMPLE VIII 4,4"-Dicarboxy-4'-methyl-triphenylamine

In a 100 ml round-bottomed flask were placed 4,4'-dicyano-4"-methyltriphenylamine triphenylamine (5.00 g, 16.16 mmol.) and potassium hydroxide (3.62 g., 64.64 mmol.) and 40 ml of ethylene glycol. The resultant slurry was heated at reflux for 16 h. During reflux, the reaction mixture became completely clear and yellow. The final yellow solution was cooled, poured over ice, and neutralized with 3 N hydrochloric acid. The off-white, flaky solid was isolated by filtration, dried and recrystallized from aqueous methanol to provide the desired diacid as off-white platelets. Yield: 4.60 g (80%), m.p. 188°–190° C. Elemental Analysis for $C_{21}H_{17}NO_4$: Calcd.: C, 72.61%; H, 4.93%; N, 4.03%. Found: C, 72.48%; H, 4.87%; N, 4.00%. IR (cm$^-$, KBr): 3500-2500 (OH), 1690 (C=O). Mass Spectrum: m/e:347 (M$^+$, 100%).

EXAMPLE IX

Preparation of 4,4'-Dicyanodiphenylamine (DPA) in DMSO

In a single neck round bottom flask was equipped with a magnetic stirrer was placed 4-aminobenzonitrile (15.00 g, 126.90 mmol), 4-fluorobenzonitrile (15.37 g, 126.90 mmol) and dimethylsulfoxide (DMSO, 100 ml). The flask was fitted with a condenser, nitrogen inlet and outlet. To the solution was added potassium tert-butoxide (28.49 g, 253.90 mmol) in five: portions. The solution turned to reddish-brown and was stirred at room temperature for 16 hours. The brown solution was poured over ice, neutralized with dilute hydrochloric acid (HCl, 2 N). The yellow precipitate was filtered, washed several times with water and dried. The crude solid was recrystallized from acetonitrile to obtain light yellow needles. Yield: 11.45 g (46%). top: 248°–250° C. Infrared (KBr, in cm$^{-1}$): 3367 (vNH); 2218 (vCN). $^1$HNMR (270 MHz; DMSO-d$_6$, d values in ppm): 7.26, 7.29 (aromatic protons ortho to NH function, J=8.8 Hz); 7.70, 7.73 (aromatic protons ortho to CN function; J=8.8 Hz ); 9.49 (NH). $^{13}$C NMR (DMSO-d$_6$, d values in ppm): 102.20 (phenyl carbon bearing CN group); 117.34 (phenyl carbon ortho to NH group); 119.48 (CN carbon); 133.76 (phenyl carbon ortho to CN group); 145.79 (phenyl carbon bearing NH group). (Mass spectrum: m/e: 219 (M$^+$).

EXAMPLE X

Preparation of 4,4"-Dicyanodiphenylamine (DPA) in DMAc

In a single neck round bottom flask was placed 4-aminobenzonitrile (6.00 g, 50.78 mmol), 4-fluorobenzonitrile (6.15 g, 50.78 mmol) and N,N-dimethylacetamide (50 ml). The flask was fitted with a condenser and a magnetic stirrer and stirred under nitrogen. To the light yellow solution, potassium tert-butoxide (8.54 g, 76.18 mmol) was added in two portions. Immediately and exothermically, the reaction mixture became reddish-brown. The solution was stirred at room temperature for 16 hours. The reddish-black solution was poured into water to precipitate an off-white solid, and the resultant mixture was then neutralized with aqueous 2N HCl. The off-white crude product was collected on a fritted funnel, washed with distilled water and dried overnight with suction. It was subsequently purified by recrystallization from acetonitrile (or methanol), resulting in light yellow-green needles. Yield: 5.00 g (45%). top: 259°–261° C. [Lit. mp:256°–260° C.]. Infrared (KBr, in cm$^{-1}$): 3367 (vNH); 2218 (vCN). $^1$HNMR (270 MHz; DMSO-d$_6$, d values in ppm): 7.26, 7.29 (aromatic protons ortho to NH function, J=8.8 Hz); 7.70, 7.73 (aromatic protons ortho to CN function; J=8.8 Hz ); 9.49 (NH). $^{13}$C NMR (DMSO-d$_6$, d values in ppm): 102.20 (phenyl carbon bearing CN group); 117.34 (phenyl carbon ortho to NH group); 119.48 (CN carbon); 133.76 (phenyl carbon ortho to CN group); 145.79 (phenyl carbon bearing NH group). Mass spectrum: m/e: 219 (M$^+$).

EXAMPLE XI

Preparation of 4,4"-Dicyanodiphenylamine (DPA) in DMF

In a single neck round bottom flask was equipped with a magnetic stirrer was placed 4-aminobenzonitrile (5.00 g, 42.32 mmol.), 4-fluorobenzonitrile (5.13 g, 42.32 mmol.) and N, N-dimethylformamide (DMF, 100 ml). The flask was fitted with a condenser, nitrogen inlet and outlet. To the solution was added potassium tert-butoxide (9.50 g, 84.64 mmol.) in five portions. The solution turned to reddish-brown and was stirred at room temperature for 12 h. The dark brown solution was poured over ice (500 ml), neutralized with dilute hydrochloric acid (HCl, 2 N). The light pink precipitate was filtered, washed several times with water and dried. The crude solid (6.9 g,) was recrystallized from acetonitrile to obtain light pink needles. Yield: 4.30 g (46%). top: 254°–256° C. Infrared (KBr, in cm$^{-1}$): 3367 (vNH); 2218 (vCN). $^1$HNMR (270 MHz; DMSO-d$_6$, d values in ppm): 7.26, 7.29 (aromatic protons ortho to NH function, J=8.8 Hz); 7.70, 7.73 (aromatic protons ortho to CN function; J=8.8 Hz ); 9.49 (NH). $^{13}$C NMR (DMSO-d$_6$, d values in ppm): 102.20 (phenyl carbon bearing CN group); 117.34 (phenyl carbon ortho to NH group); 119.48 (CN carbon); 133.76 (phenyl carbon ortho to CN group); 145.79 (phenyl carbon bearing NH group). Mass spectrum: m/e: 219 (M$^+$).

EXAMPLE XII

Preparation of 4,4'-Dicyanodiphenylamine (DPA) in NMP

In a single neck round bottom flask equipped with a magnetic stirrer was placed 4-aminobenzonitrile (5.00 g, 42.32 mmol.), 4-fluorobenzonitrile (5.13 g, 42.32 mmol.) and N-methylpyrrolidinone (NMP, 100 ml). The flask was fitted with a condenser, nitrogen inlet and outlet. To the solution was added potassium tert-butoxide (9.50 g, 84.64 mmol.) in five portions. The solution turned to reddish-brown and was stirred at room temperature for 12 h. The dark brown solution was poured over ice (500 ml), neutralized with dilute hydrochloric acid (HCl, 2 N). The yellow precipitate was filtered, washed several times with water and dried. The crude solid (7.16 g,) was recrystallized from acetonitrile to obtain light yellow powder. Yield: 4.10g (44%). mp: 254°–256° C. Infrared (KBr, in cm$^{-1}$): 3367 (vNH); 2218 (vCN). $^1$HNMR (270 MHz; DMSO-d$_6$, d values in ppm): 7.26, 7.29 (aromatic protons ortho to NH function, J=8.8 Hz); 7.70, 7.73 (aromatic protons ortho to CN function; J=8.8 Hz ); 9.49 (NH). $^{13}$C NMR (DMSO-d$_6$, d values in ppm): 102.20 (phenyl carbon bearing CN group); 117.34 (phenyl carbon ortho to NH group); 119.48 (CN carbon); 133.76 (phenyl carbon ortho to CN group); 145.79 (phenyl carbon bearing NH group). Mass spectrum: m/e: 219 (M$^+$).

EXAMPLE XIII

4,4'-Dicarboxydiphenylamine (DPA(CO$_2$H)$_2$

In a 100 ml single-neck, round-bottomed flask was placed 4,4'-dicyanodiphenylamine (12.00 g, 54.70 mmol), potassium hydroxide pellets (12.40 g, 219.0 mmol) and ethylene glycol (70 ml). The yellow slurry was stirred under nitrogen with a magnetic stirrer, and heated at reflux for 16 h. The clear brown solution was cooled to room temperature, diluted with water (100 ml) and neutralized with aqueous hydrochloric acid (4 N). The yellow precipitate was filtered and the resulting yellow solid washed several times with water (200 ml). The crude product was recrystallized from a mixture of dimethylacetamide-water to obtain an off-white crystalline solid. Yield: 12.50 g (89%). mp: 337°–340° C. Mass spectral: m/e: 257 (M+). IR (KBr, cm$^{-1}$): 3319 (vNH); 3300-2400 (vOH); 1677 (vC=O). Elemental Anal. Calcd. for $C_{14}H_{11}NO_4$: C, 65.36%; H, 4.31%; N, 5.44%. Found: C, 65.28%; H, 4.28%; N, 5.34%.

EXAMPLE XIV

Preparation of Poly[benzo[1,2-d'4,5-d']bisthiazole-2,6-diyl-1,4-phenylene-imino-1,4-phenylene](DPA-PBZT) using 4,4'-dicyanodiphenyl amine prepared in DMSO In a four neck reaction flask was accurately weighed 4,4'-dicyanodiphenyl amine (1.4000 g, 6.385 mmol), 2,5-diamino-1,4-phenylenedithiol dihydrochloride (1.5657 g, 6.385 mmol) and 77% polyphosphoric acid (PPA, 13.18 g). The flask was fitted with a mechanical stirrer and deaerated with nitrogen. The light yellow reaction mixture was stirred under positive nitrogen pressure. The mixture was then heated to 45° C., under vacuum. The reddish orange solution was stirred at 60° C. for 48 h. After the completion of degassing, the dark red mixture was cooled and 99.9% phosphorus pentoxide ($P_2O_5$, 6.89 g) was added to adjust the $P_2O_5$ content of PPA medium to 83%. The light red solution was then slowly heated and stirred at 100° C. for 4 h; at 120° C. for 16 h, at 130° C. for 2 h and 140° C. for 1 h. The polymerization mixture was worked up by pouring into water and the precipitated polymer was shredded in a high speed blender. The polymer collected was subsequently neutralized with 10% aqueous $NH_4OH$, washed and soxhlet extracted with water for 24 h, filtered and dried under vacuum at 100° C. for 24 h. Yield: 2.03 g (86%). [η]=1.32 dL/g (methanesulfonic acid, 30° C.). Elemental Anal. Calcd. for $C_{20}H_{11}N_3S_2$: C, 67.20%; H, 3.10%; N, 11.76%. Found: C, 60.80%; H, 3.00%; N, 9.89%.

EXAMPLE XV

Preparation of Poly[benzo[1,2-d:4,5-d']bisthiazole-2,6-diyl-1,4-phenylene-imino-1,4-phenylene] (DPA-PBZT) using 4,4'-dicyanodiphenylamine prepared in DMAc In a four neck reaction flask was accurately weighed 4,4'-dicyanodiphenyl amine (1.4000 g, 6.385 mmol), 2,5-diamino-1,4-phenylenedithiol dihydrochloride (1.5657 g, 6.385 mmol) and 77% polyphosphoric acid (PPA, 13.18 g). The flask was fitted with a mechanical stirrer and deaerated with nitrogen. The light yellow reaction mixture was stirred under positive nitrogen pressure. The mixture was then heated to 45° C., under vacuum. The reddish orange solution was stirred at 60° C. for 48 h. After the completion of degassing, the dark red mixture was cooled and 99.9% phosphorus pentoxide ($P_2O_5$, 6.89 g) was added to adjust the $P_2O_5$ content of PPA medium to 83%. The light red solution was then slowly heated and stirred at 100° C. for 4 h; at 120° C. for 16 h, at 130° C. for 2 h and 140° C. for 1 h. The polymerization mixture was worked up by pouring into water and the precipitated polymer was shredded in a high speed blender. The polymer collected was subsequently neutralized with 10% aqueous $NH_4OH$, washed and soxhlet extracted with water for 24 h, filtered and dried under vacuum at 100° C. for 24 h. Yield: 2.03 g (86%). [η]=3.18 dL/g (methanesulfonic acid, 30° C.). Elemental Anal. Calcd. for $C_{20}H_{11}N_3S_2$: C, 67.20%; H, 3.10%; N, 11.76%. Found: C, 66.80%; H, 3.00%; N, 11.49%.

Comparison of the intrinsic viscosity (η) of the polymer prepared in this Example with that of the polymer prepared in Example XIV reveals that the solvent employed in the preparation of the 4,4'-dicyanodiphenylamine has considerable effect on the intrinsic viscosity.

EXAMPLE XVI

Preparation of Poly[benzo[1,2-d:4,5-d']bisthiazole-2,6-diyl-1,4-phenylene-imino-1,4-phenylene]/[benzo[1,2-d:4,5-d'}bisthiazole-2,6-diyl-1,4-phenylene]](10:90 mol %) using 4,4'-dicyanodiphenyl amine prepared in DMSO In a four neck reaction flask was accurately weighed 4,4'-dicyanodiphenyl amine (0.1259 g., 0.4894 mmol.), terephthalic acid (0.7318 g, 4.4046 mmol.), 2,5-diamino-1,4-phenylenedithiol dihydrochloride (1.2000 g, 4.8940 mmol.) and 77% polyphosphoric acid (PPA, 7.43 g). The flask was fitted with a mechanical stirrer and deaerated with nitrogen. The yellow solution was stirred at 45° C. for 2 h, and at 50° C. for 16 h. The light orange solution was further heated and stirred at 80° C. for 1 h, at 100° C. for 1 h and 120° C. for 16 h, cooled the reddish-orange solution to about 50° C. and $P_2O_5$ (4.34 g) was added. The slightly reddish-orange solution was warmed to 100° C. over 3 h and stirred at 120° C. for 1 h, at 130° C. for 3 h, at 150° C. for 16 h and at 160° C. for 4 h. The final dark viscous stir-opalescent solution was allowed to cool to about 50° C. and poured in water. The precipitated polymer was shredded in a high-speed blender, neutralized with aqueous ammonium hydroxide, and washed with boiling water for 16 h. The light red polymer was filtered and dried under vacuum at 110° C. over $P_2O_5$ for 24 h. Yield: 1.28 g. (96%). [η]=1.62 dL/g (MSA). Elemental Anal. Calcd. C, 63.66%; H, 2.38%; N, 10.68%. Found: C, 60.03%; H, 1.96%; N, 10.03%.

EXAMPLE XVII

Preparation of Poly[benzo[1,2-d:4,5-d']bisthiazole-2,6-diyl-1,4-phenylene-imino-1,4-phenylene]/[benzo[1,2-d:4,5-d'}bisthiazole-2,6-diyl-1,4-phenylene]] (10:90 mol %) using 4,4'-dicyanodiphenyl amine prepared in DMAc In a four neck reaction flask was accurately weighed 4,4'-dicyanodiphenyl amine (0.1609 g, 0.734 mmol), terephthalic acid (1.0976 g, 6.607 mmol), 2,5-diamino-1,4-phenylenedithiol dihydrochloride (1.8000 g, 7.34 mmol) and 77% polyphosphoric acid (PPA, 13.18 g). The flask was fitted with a mechanical stirrer and deaerated with nitrogen. The yellow solution was stirred at 45° C. for 2 h, and at 50° C. for 16 h. The light orange solution was further heated and stirred at 80° C. for 1 h, at 100° C. for 1 h and 120° C. for 16 h, cooled the reddish-orange solution to about 50° C. and $P_2O_5$ (6.52 g) was added. The slightly reddish-orange solution was warmed to 100° C. over 3 h and stirred at 120° C. for 1 h, at 130° C. for 3 h, at 150° C. for 16 h and at 160° C. for 4 h. The final dark viscous stir-opalescent solution was allowed to cool to about 50° C. and poured in water. The precipitated polymer was shredded in a high-speed blender, neutralized with aqueous ammonium hydroxide, and washed with boiling water for 16 h. The light red polymer was filtered and dried under vacuum at 110° C. over $P_2O_5$ for 24 h. Yield: 1.943 g (80%). [η]=13.80 dL/g (MSA). Elemental Anal. Calcd. C, 63.66%; H, 2.38%; N, 10.68%. Found: C, 62.86%; H, 2.58%; N, 8.94%.

Comparison of the intrinsic viscosity (η) of the copolymer prepared in this Example with that of the copolymer prepared in Example XVI reveals that the solvent employed in the preparation of the 4,4'-dicyanodiphenyl amine has considerable effect on the intrinsic viscosity. Under virtually identical reaction conditions, the use of a sulfur-free solvent in the preparation of the 4,4'-dicyanodiphenyl amine resulted in a greater than eight-fold increase in intrinsic viscosity of the copolymer.

EXAMPLE XVIII

Poly[benzo[1,2-d:4,5-d']bisoxazole-2,6-diyl-1,4-phenylene-imino-1,4-phenylene] (DPA-PBO)

In a four neck reaction flask was accurately weighed 4,4'-dicyanodiphenylamine, (1.5000 g, 6.841 mmol), 2,4-diamino-1,5-benzenediol dihydrochloride (1.4577 g, 6.841 mmol) and 77% polyphosphoric acid (PPA, 9.92 g). The flask was fitted with a mechanical stirrer and deaerated with nitrogen. The light yellow reaction mixture was stirred under positive nitrogen pressure. The yellow mixture was then heated to 45° C. for 16 h and at 75° C. for 4 h. and at 110° C. for 16 h. After the completion of degassing, the dark mixture was cooled to 50° C. and phosphorus pentoxide ($P_2O_5$, 5.91 g) was added. The green-black solution was then heated and stirred at 110° C. for 16 h, at 120° C. for 2 h and 140° C. for 4 h. The green-black dope was cooled to 60° C. and poured into water. The dark green polymer was dried under vacuum at 110° C. for 24 h. Yield: 2.01 g (90%). [η]=0.51 dL/g (methanesulfonic acid, 30° C.). Elemental Anal. Calcd. for $C_{20}H_{11}N_3O_2$: C, 73.84%; H, 3.41%; N, 12.92%. Found: C, 60.39%; H, 3.11%; N, 10.63%.

EXAMPLE XIX

Preparation of Poly[benzo[1,2-d:4,5-d']bisimidazole-2,6-diyl-1,4-phenylene-imino-1,4-phenylene] (DPA-PDI)

In a four neck reaction flask was accurately weighed 4,4'-dicyanodiphenylamine, (1.5000 g, 6.841 mmol), 1,2,4,5-tetraminobenzene tetrahydrochloride (1.9431 g, 6.841 mmol) and 77% polyphosphoric acid (12.57 g). The flask was fitted with a mechanical stirrer and deaerated with nitrogen. The light yellow reaction mixture was stirred under positive nitrogen pressure. The yellow mixture was then heated to 45° C. for 16 h and at 75° C. for 4 h (golden yellow) and at 110° C. for 16 h. After the completion of degassing, the dark mixture was cooled to 50° C. and phosphorus pentoxide ($P_2O_5$, 6.84 g) was added. The green-black solution was then heated and stirred at 110° C. for 16 h, at 120° C. for 2 h and 140° C. for 4 h. The green-black dope was cooled to 60° C. and poured into water. The precipitated polymer was collected by filtration, followed by neutralization with 10% aqueous $NH_4OH$, washing and finally, soxhlet-extraction with water for 24 h. The dark green polymer was dried under vacuum at 110° C. for 24 h. Yield: 1.973 g (89%). [η]=0.68 dL/g (methanesulfonic acid, 30° C.). Elemental Anal. Calcd. for $C_{20}H_{13}N_5$: C, 74.29%; H, 4.05%; N, 21.66%. Found: C, 69.64%; H, 4.32%; N, 20.72%.

EXAMPLE XX

Conductivity Measurements

For conductivity measurements, films were cast from dilute methanesulfonic acid (MSA) solutions (<4% w/w) at 60° C. under vacuum. The cast films were washed with methanol, water, 5% aq. $NH_4OH$, water and subsequently dried at 100° C. under reduced pressure for 24 h. Activation of the films was carried out by exposing them to iodine vapor for 16 h at room temperature. In all cases, the films showed a color change from light red-brown to metallic black. The conductivity data of the pristine (undoped) and iodine-doped copolymer films were determined using the standard 4-point probe method.

All the copolymers at their pristine state were insulators with conductivity values of less than $10^{-10}$ S/cm, which is below the detection limit for the film thickness of the samples. However, upon exposure to iodine vapor at room temperature for 16 hours, the doped copolymer films exhibited immediate increases in their conductivity of at least five to seven orders of magnitude Table I, below, shows the conductivities of undoped (pristine) and iodine-doped films of the copolymer of Example XVII, as well as two other copolymers prepared using the procedure of Example XVII.

TABLE I

| x | 1 − x | Polym. Conc. w/w | Reaction Temp (°C.)/Time | [η] (MSA, 30° C., dL/g) | Conductivity, S/cm | |
|---|---|---|---|---|---|---|
| | | | | | Pristine | $I_2$-doped |
| 0.1 | 0.9 | 10% | 145(2 h) | 13.80 | <$10^{-10}$ | $2.0 \times 10^{-5}$ |
| 0.3 | 0.7 | 10% | 145(1 h) | 6.20 | <$10^{-10}$ | $1.7 \times 10^{-4}$ |
| 0.5 | 0.5 | 10% | 150(2 h) | 6.10 | <$10^{-10}$ | $9.6 \times 10^{-4}$ |

Various modifications may be made in the instant invention without departing from the., spirit and scope of the appended claims.

We claim:

1. A polymer having repeating units of the formula:

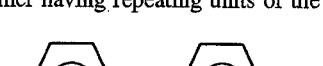

wherein Q is

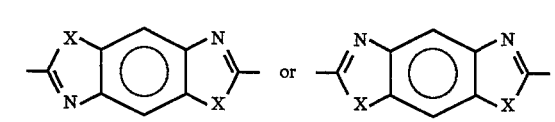

wherein X is —NH—, —S— or —O—.

2. The polymer of claim 1 wherein X is —S—.

3. The polymer of claim 1 wherein X is —O—.

4. The polymer of claim 1 wherein X is —NH—.
5. A copolymer having repeating units of the formula:
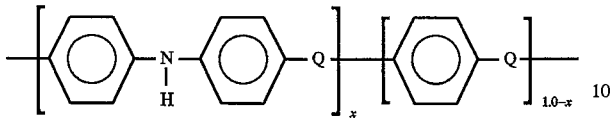
wherein x has a value of 0.01 to 0.99 and Q is
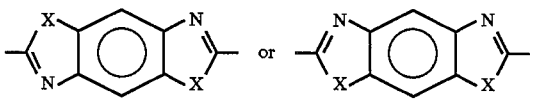
wherein X is —NH—, —S— or —O—.
6. The copolymer of claim 1 wherein X is —S—.
7. The copolymer of claim 1 wherein X is —O—.
8. The copolymer of claim 1 wherein X is —NH—.
* * * * *